United States Patent [19]

Schenttler et al.

[11] Patent Number: 4,670,450

[45] Date of Patent: Jun. 2, 1987

[54] CARDIOTONIC THIAZOLONES

[75] Inventors: Richard A. Schenttler; Winton D. Jones, Jr.; George P. Claxton, all of Cincinnati, Ohio

[73] Assignee: Merrell Dow Pharmaceuticals Inc., Cincinnati, Ohio

[21] Appl. No.: 797,579

[22] Filed: Nov. 13, 1985

[51] Int. Cl.$^4$ .................. C07D 277/04; C07D 277/12; C07D 277/34; C07D 409/00

[52] U.S. Cl. ............................... 514/341; 548/182; 548/189; 548/186; 546/280; 546/278; 514/342; 514/369

[58] Field of Search ............. 548/182, 189, 186; 546/280, 278; 514/342, 341, 369, 787, 276, 786, 984, 787, 226

[56] References Cited

U.S. PATENT DOCUMENTS

| | | | |
|---|---|---|---|
| 3,897,410 | 4/1975 | Bottari et al. | 548/182 |
| 4,188,323 | 2/1980 | Pestellini et al. | 548/182 |
| 4,418,070 | 11/1983 | Okonogi et al. | 548/182 |
| 4,532,250 | 7/1985 | Stout et al. | 548/182 |
| 4,623,651 | 11/1986 | Grisar et al. | 514/342 |

FOREIGN PATENT DOCUMENTS

| | | | |
|---|---|---|---|
| 0117082 | 8/1984 | European Pat. Off. | 548/182 |
| 7654553 | 11/1974 | Japan | 548/182 |
| 51-11763 | 1/1976 | Japan | 548/182 |
| 1305273 | 1/1973 | United Kingdom | 548/182 |
| 427015 | 12/1974 | U.S.S.R. | 548/182 |

OTHER PUBLICATIONS

Nakagawa M., et al., Agric. Biol. Chem. 38(11):2205-8 (1974).
Nakagawa M. et al., Agric. Biol. Chem. 39(9):1763-73 (1975).
Fukumi H. et al., Heterocycles 12(10):1297-9 (1979).
Shvaika O. P., Klimisha GP. Dopov. Akad. Nauk Ukr. RSR, Ser. B 32(4):350-2 (1970).
Bottari F., et al., J. Med Chem. 15(1):39-42 (1972).
Roderhorst RM, Koch TH. J. Am. Chem. Soc. 97(25):7298-304 (1975).
Saettorne MF, et al., Gazz. Chim. Ital. 96(11):1615-29 (1966).
Krieg B., Konieczny P. Justus Liebigs Ann. Chem. (10: 1862-72 (1976).
Dziomko VA, Ivashchenko AV, ZH. Org, Khim. 9(10):2191-4 (1973).
J. Pharm. Soc. Japan 72:1017-20, 1952, Yuichi Yamamoto: Studies on Chemotherapeutics for Acid-Fast Bacilli. III., Antibacterial Activity of Some Thiazole and Pyridine Derivatives.

*Primary Examiner*—John M. Ford
*Assistant Examiner*—Robert C. Whittenbaugh
*Attorney, Agent, or Firm*—Stephen L. Nesbitt

[57] ABSTRACT

Thiazolones enhance myocardial contractile force and are useful as cardiotonics in the treatment of heart failure.

18 Claims, No Drawings

CARDIOTONIC THIAZOLONES

BACKGROUND OF THE INVENTION

This invention relates to the use of certain thiazolones to enhance myocardial contractile force. These compounds are useful as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea and pulmonary edema.

Treatment involves either removal or correction of the underlying cause or involves control of the heart failure state. Management or control can be accomplished by increasing cardiac output or by decreasing cardiac workload. While workload can be reduced by reduction of physical activities and physical and emotional rest, increasing cardiac output has traditionally involved therapy with digitalis or a digitalis glycoside and more recently vasodilator therapy. Digitalis stimulates contractile force of the heart which increases cardiac output and improves ventricular emptying. In this way digitalis therapy normalizes venous pressure and reduces peripheral vasoconstriction, circulatory congestion and organ hypoperfusion Unfortunately, optimal doses of digitalis vary with the patient's age, size and condition and the therapeutic to toxic ratio is quite narrow. In most patients the lethal dose is only about five to ten times the minimal effective dose with toxic effects becoming apparent at only 1.5 to 2.0 times the efective dose. For these reasons, dose must be carefully tailored to suit the individual and frequent clinical examination and electrocardiogram are necessary to detect early signs of digitalis intoxication. Despite this care digitalis intoxication is reported in up to one-fifth of hospitalized patients undergoing therapy.

Vasodilator therapy increases cardiac output and improves ventricular emptying by reducing the systemic blood pressure against which the heart must pump. However, in severe heart failure a vasodilator alone may not improve cardiac function sufficiently due to the weakness of the myocardial contractility necessitating the concomitant use of digitalis. Moreover, a rapid tolerance has been reported to develop to the effects of vasodilator therapy in heart patients. The need for less toxic and more effective cardiotonic agents is readily apparent. Applicants have discovered certain phenyl thiazolones which possess potent cardiotonic activity and by comparison to digitalis have few toxic effects.

SUMMARY OF THE INVENTION

This invention is directed to thiazolones of formula 1

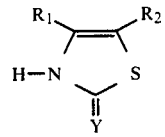

wherein
Y is an oxygen or sulfur group;
$R_1$ is a hydrogen or a ($C_1$–$C_5$) alkyl group when $R_2$ is R;
$R_2$ is a hydrogen or a ($C_1$–$C_5$) alkyl group when $R_1$ is R; and
R is a phenyl group optionally substituted with one or two members of the group consisting of ($C_1$–$C_5$) alkyl, ($C_1$–$C_5$) alkoxy, ($C_1$–$C_5$) alkylthio, ($C_1$–$C_5$)alkylsulfinyl, ($C_1$–$C_5$) alkylsulfonyl, hydroxy, halogen, cyano, carboxy, carb($C_1$–$C_5$) alkoxy, ($C_1$–$C_5$) alkanoylamino, imidazolyl or trifluoromethyl, or with a methylenedioxy group; or a 2-, 3- or 4-pyridyl group optionally substituted with a hydroxy, halogen, ($C_1$–$C_5$) alkyl, ($C_1$–$C_5$) alkoxy, ($C_1$–$C_5$) alkylthio, ($C_1$–$C_5$) alkylsulfinyl, ($C_1$–$C_5$) alkylsulfonyl, cyano, carboxy, carb($C_1$–$C_5$) alkoxy, ($C_1$–$C_5$) alkanoylamino, or imidazolyl; or R is or a 2- or 3- furanyl, 2- or 3- thienyl or 2- or 3- pyranyl group.

These compounds enhance myocardial contractile force and are useful as cardiotonics in the treatment of heart failure.

DETAILED DESCRIPTION OF THE INVENTION

The formula 1 compounds exist in several tautomeric forms. Throughout this disclosure, thiazolones of formula 1 are intended to include these tautomers as well.

The ring nitrogen of the formula 1 compounds can be substituted with a ($C_{1-C5}$) alkyl group, an alkanoyl group such as an acetyl group, or a benzoyl group. These nitrogen substituted compounds are equivalent to the unsubstituted compounds primarily because the substituent is cleaved upon administration to a patient but also because many of the nitrogen substituted compounds independently possess significant ability to enhance myocardial contractile force and are useful cardiotonic agents.

As used herein the term ($C_1$–$C_5$) alkyl and the alkyl portion of the alkoxy, alkylthio, alkylsulfinyl, alkylsulfonyl, carbalkoxy, and alkanoylamino groups means a straight or branched alkyl group of from one to five carbon atoms. Illustrative examples of ($C_1$–$C_5$) alkyl group are methyl, ethyl, isopropyl, butyl, sec-butyl and pentyl. The term halogen means a fluoro, chloro, bromo or iodo group. Imidazolyl means a 1-, 2-, 3-, 4- or 5-imidazolyl.

As is true for most classes of therapeutically effective compounds, certain subclasses are more effective than others. In this instance those compounds of formula 1 wherein Y is an oxo qroup are preferred. Also preferred are those compounds wherein $R_1$ is a ($C_1$–$C_5$) alkyl group or wherein $R_2$ is a ($C_1$–$C_5$) alkyl group. More preferred are those compounds of formula 1 wherein $R_1$ is a ($C_1$–$C_5$) alkyl group. And $R_2$ is an optionally substituted phenyl or optionally substituted pyridyl. The most preferred compounds of formula 1 are those wherein $R_1$ is a methyl, ethyl or propyl group and wherein $R_2$ is an unsubstituted phenyl group or unsubstituted 4-pyridyl.

The compounds of formula 1 can be prepared by standard techniques analagously known in the art.

In one procedure a bromoketone of formula 2A or 2B

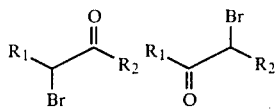

2A    2B wherein $R_1$ and $R_2$ are as defined above is allowed to react with a sulfhydride salt, such as sodium sulfhydride or preferably a sulfhydride equivalent, such as 1-acetyl-2-thiourea to form a mercaptan of formula 3A or 3B

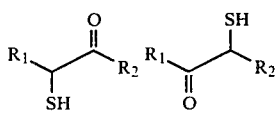

3A    3B wherein $R_1$ and $R_2$ are as defined above. Subsequent reaction with a cyanate or thiocyanate salt results in a thiazolone of formula 1. Sulfhydride equivalents can be prepared in situ by reaction of, for example, sodium or potassium sulfide with an aqueous base solution such as an aqueous sodium hydroxide solution.

The bromo-ketones of formula 2A and 2B are either known in the art or can be readily prepared by standard techniques. For example the des-bromo analog of a structure 2A or 2B compound can be treated with bromine. Where the group adjacent to the carbon to be brominated is a hydrogen or a ($C_1$–$C_5$) alkyl group, a radical initiator can be used to promote the bromination. Suitable initiators include iron metal and N-bromosuccinimide. The bromination can also be accomplished by addition of concentrated hydrobromic acid, typically 48% aqueous hydrobromic acid, to a solution containing the des-bromo compound.

The compounds of formula 1 are cardiotonic agents useful in the treatment of heart failure. The utility of formula 1 compounds as cardiotonics may be determined by administering the test compound (0.1–100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or left ventricle of the heart to record left atrial pressure or left ventricular pressure. Heart failure is induced by administering sodium pentobarbital (20 to 40 mg/kg) followed by a continuous infusion of 0.25–2 mg/kg/min. or propranalol hydrochloride (4 mg/kg) followed by a continuous infusion of 0.18 mg/kg/min. to the blood perfusing the heart. Following administration of either of these cardiac depressants, the left atrial pressure dramatically increases and cardiac output is severly depressed. Reversal of these effects by the test compound indicates cardiotonic activity.

The compounds may be administered in various manners to achieve the desired effect. The compound may be administered alone or in the form of pharmaceutical preparations to the patient being treated either topically, orally or parenterally, that is, intravenously or intramuscularly. The amount of compound administered will vary with the patient, the severity of the cardiac failure and the mode of administration.

For topical, oral or parenteral administration the cardiotonically effective amount of compound and the amount required to enhance myocardial contractile force is from about 0.1 mg/kg of patients body weight per day up to about 400 mg/kg of patient body weight per day and preferably from about 0.3 mg/kg of patient body weight per day up to about 120 mg/kg of patient body weight per day.

For oral administration a unit dosage may contain, for example, from 5 to 700 mg of the active ingredient, preferably about 15 to 500 mg of the active ingredient. For parenteral administration a unit dosage may contain, for example, from 5 to 700 mg of the active ingredient, preferably about 15 to 210 mg. Repetitive daily administration of the compounds may be desired and will vary with the condition of the patient and the mode of administration.

As used herein, the term "patient" is taken to mean warm blooded animals, for example, birds, such as chickens and turkeys, and mammals, such as sheep, horses, bovine cows and bulls, pigs, dogs, cats, rats, mice and primates, including humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

The following specific examples further illustrate the preparation and use of the compounds of formula 1 but are not intended to limit the scope of the invention.

EXAMPLE 1

4-Ethyl-5-pyridin-4-yl-2(3H)thiazolone 1-(4-Pyridyl)-1-bromo-2-butanone (28.8 g, 0.1 mol) and 1-acetyl-2-thiourea (13.0 g, 0.11 mol) are combined in 200 ml absolute ethanol and refluxed 24 hours. The solvent is evaporated and the residue is purified by chromatography. The thiol is mixed with (8.1 g, 0.1 mol) potassium cyanate and 0.2 mol 10% aqueous hydrochloric acid. The mixture is heated to 80° C. for 15 minutes, then cooled. The acid is adjusted to ph=6.5 with solid sodium bicarbonate which causes the product to precipitate.

EXAMPLE 2

A tablet is prepared from

| | |
|---|---|
| 4-ethyl-5-pyridin-4-yl-2(3H)thiazolone | 250 mg |
| starch | 40 mg |
| talc | 10 mg |
| magnesium stearate | 10 mg |

EXAMPLE 3

A capsule is prepared from

| | |
|---|---|
| 4-propyl-5-phenyl-2(3H)thiazolone | 400 mg |
| talc | 40 mg |
| sodium carboxymethylcellulose | 40 mg |
| starch | 120 mg |

What we claim is:

1. A thiazolone of the formula

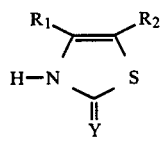

wherein
Y is an oxygen or sulfur group;
$R_1$ is a hydrogen or a ($C_1$–$C_5$) group where $R_2$ is R;
$R_2$ is a hydrogen or a ($C_1$–$C_5$) group where $R_1$ is R; and
R is a phenyl group substituted with one or two members of the group consisting of ($C_1$–$C_5$) alkyl, ($C_1$–$C_5$) alkoxy, ($C_1$–$C_5$) alkylthio, ($C_1$–$C_5$) alkylsulfinyl, ($C_1$–$C_5$)alkylsulfonyl, hydroxy, halogen, cyano, carboxy, carb($C_1$–$C_5$)alkoxy, ($C_1$–$C_5$) alkanoylamino, imidazolyl or trifluoromethyl, or with a methylenedioxy group; or a 2-, 3- or 4- pyridyl group optionally substituted with a hydroxy, halogen, ($C_1$–$C_5$) alkyl, ($C_1$–$C_5$) alkoxy, ($C_1$–$C_5$) alkylthio, ($C_1$–$C_5$) alkylsulfinyl, ($C_1$–$C_5$) alkylsulfonyl, cyano, carboxy, carb($C_1$–$C_5$) alkoxy, ($C_1$–$C_5$)alkanoylamino, imidazolyl, or R is a 2- or 3- furanyl, 2- or 3- thienyl or 2- or 3-pyranyl group.

2. A thiazolone of claim 1 wherein Y is an oxygen group.

3. A thiazolone of claim 2 wherein $R_1$ or $R_2$ is a ($C_1$–$C_5$) alkyl group.

4. A thiazolone of claim 2 wherein $R_2$ is an optionally substituted phenyl or optionally substituted pyridyl group.

5. A thiazolone of claim 2 wherein $R_1$ is a methyl, ethyl or propyl group.

6. A thiazolone of claim 5 wherein $R_2$ is an unsubstituted phenyl group or unsubstituted 4-pyridyl group.

7. A method of treating heart failure in a patient in need thereof which comprises administering to the patient a cardiotonically effective amount of a thiazolone of claim 1.

8. A method of claim 7 wherein Y is an oxygen group.

9. A method of claim 8 wherein $R_1$ or $R_2$ is a ($C_1$–$C_5$) alkyl group.

10. A method of claim 8 wherein $R_2$ is an optionally substituted phenyl or optionally substituted pyridyl group.

11. A method of claim 8 wherein $R_1$ is a methyl, ethyl or propyl group.

12. A method of claim 11 wherein $R_2$ is an unsubstituted phenyl group or unsubstituted 4-pyridyl group.

13. A method of enhancing myocardial contractile force in a patient in need thereof which comprises administering to the patient an effective amount of a method of claim 1.

14. A method of claim 13 wherein Y is an oxygen group.

15. A method of claim 14 wherein $R_1$ or $R_2$ is a ($C_1$–$C_5$) alkyl group.

16. A method of claim 14 wherein $R_2$ is an optionally substituted phenyl or optionally substituted pyridyl group.

17. A method of claim 14 wherein $R_1$ is a methyl, ethyl or propyl group.

18. A method of claim 17 wherein $R_2$ is an unsubstituted phenyl group or unsubstituted 4-pyridyl group.

* * * * *